(12) United States Patent
Pillai et al.

(10) Patent No.: US 12,053,602 B2
(45) Date of Patent: Aug. 6, 2024

(54) METHODS AND DEVICES FOR VASCULAR ACCESS

(71) Applicant: Vascular Access Technologies, Inc., South Jordan, UT (US)

(72) Inventors: Lakshmikumar Pillai, Morgantown, WV (US); Mark Henry Wholey, Pittsburgh, PA (US)

(73) Assignee: Vascular Access Technologies, Inc., South Jordan, UT (US)

( * ) Notice: Subject to any disclaimer, the term of this patent is extended or adjusted under 35 U.S.C. 154(b) by 60 days.

(21) Appl. No.: 15/834,998

(22) Filed: Dec. 7, 2017

(65) Prior Publication Data

US 2018/0161550 A1    Jun. 14, 2018

Related U.S. Application Data

(60) Provisional application No. 62/432,359, filed on Dec. 9, 2016.

(51) Int. Cl.
*A61M 25/10*    (2013.01)
*A61B 17/22*    (2006.01)
(Continued)

(52) U.S. Cl.
CPC .......... *A61M 25/104* (2013.01); *A61B 17/22* (2013.01); *A61B 17/22012* (2013.01); *A61B 17/22031* (2013.01); *A61M 25/0082* (2013.01); *A61M 25/0194* (2013.01); *A61B 2017/00252* (2013.01); *A61B 2017/00398* (2013.01); *A61B 2017/22001* (2013.01); *A61B 2017/22044* (2013.01); *A61B 2017/22094* (2013.01); *A61B 2017/22095* (2013.01);
(Continued)

(58) Field of Classification Search
CPC .... A61B 17/22012; A61B 2017/00252; A61B 2017/22001; A61B 2017/22044; A61B 2017/22095; A61M 2025/0095; A61M 2025/0197
See application file for complete search history.

(56) References Cited

U.S. PATENT DOCUMENTS

| 4,559,039 A | 12/1985 | Ash et al. |
| 4,790,825 A | 12/1988 | Bernstein et al. |
(Continued)

FOREIGN PATENT DOCUMENTS

| WO | 2004018029 | 3/2004 |
| WO | 2005053547 | 6/2005 |
(Continued)

OTHER PUBLICATIONS

Notice of Allowance dated May 1, 2019 for U.S. Appl. No. 15/347,478.
(Continued)

*Primary Examiner* — Martin T Ton
(74) *Attorney, Agent, or Firm* — Dorsey & Whitney LLP

(57) ABSTRACT

Methods and devices for treating occlusive peripheral vascular diseases are described. The devices can include an access catheter having a guidewire lumen and stylet lumen, a guide tube having a curved distal end, a stylet, and an actuator handle. The methods describe techniques for using the described devices for performing vascular procedures, such as subintimal angioplasty.

22 Claims, 13 Drawing Sheets

(51) Int. Cl.
  A61M 25/00 (2006.01)
  A61M 25/01 (2006.01)
  A61B 17/00 (2006.01)
  A61M 39/02 (2006.01)

(52) U.S. Cl.
  CPC ........... *A61M 2025/0095* (2013.01); *A61M 2025/0096* (2013.01); *A61M 2025/0197* (2013.01); *A61M 2039/0258* (2013.01)

(56) References Cited

U.S. PATENT DOCUMENTS

| | | | |
|---|---|---|---|
| 4,966,163 A | 10/1990 | Kraus et al. | |
| 5,421,348 A | 6/1995 | Larnard | |
| 5,492,530 A | 2/1996 | Fischell et al. | |
| 5,685,820 A | 11/1997 | Riek et al. | |
| 5,733,248 A | 3/1998 | Adams et al. | |
| 6,047,700 A | 4/2000 | Eggers et al. | |
| 6,102,926 A | 8/2000 | Tartaglia et al. | |
| 6,190,353 B1 | 2/2001 | Makower et al. | |
| 6,217,527 B1 | 4/2001 | Selmon et al. | |
| 6,475,226 B1 | 11/2002 | Belef et al. | |
| 6,485,513 B1 | 11/2002 | Fan | |
| 6,508,777 B1 | 1/2003 | Macoviak et al. | |
| 6,554,794 B1 | 4/2003 | Mueller et al. | |
| 6,623,480 B1 | 9/2003 | Kuo et al. | |
| 6,709,444 B1 * | 3/2004 | Makower | A61M 25/008 606/159 |
| 6,726,677 B1 * | 4/2004 | Flaherty | A61B 17/3417 604/528 |
| 6,955,657 B1 | 10/2005 | Webler | |
| 7,008,979 B2 | 3/2006 | Schottman et al. | |
| 7,374,567 B2 | 5/2008 | Heuser | |
| 7,648,517 B2 | 1/2010 | Makower et al. | |
| 8,019,420 B2 | 9/2011 | Hine et al. | |
| 8,241,311 B2 | 8/2012 | Ward et al. | |
| 8,374,680 B2 | 2/2013 | Thompson | |
| 8,409,236 B2 | 4/2013 | Pillai | |
| 8,568,435 B2 | 10/2013 | Pillai et al. | |
| 9,220,874 B2 | 12/2015 | Pillai et al. | |
| 9,282,967 B2 | 3/2016 | Paris et al. | |
| 2001/0012924 A1 | 8/2001 | Milo et al. | |
| 2001/0023346 A1 | 9/2001 | Loeb | |
| 2002/0004666 A1 | 1/2002 | Schwager et al. | |
| 2002/0029060 A1 | 3/2002 | Hogendijk et al. | |
| 2002/0120250 A1 | 8/2002 | Altman | |
| 2002/0122877 A1 | 9/2002 | Harish et al. | |
| 2002/0133168 A1 | 9/2002 | Smedley et al. | |
| 2002/0169377 A1 | 11/2002 | Khairkhahan et al. | |
| 2003/0040771 A1 | 2/2003 | Hyodoh | |
| 2004/0039371 A1 | 2/2004 | Tockman et al. | |
| 2004/0059280 A1 | 3/2004 | Makower et al. | |
| 2004/0082850 A1 | 4/2004 | Bonner et al. | |
| 2004/0097880 A1 | 5/2004 | Schur | |
| 2004/0133168 A1 | 7/2004 | Salcudean et al. | |
| 2004/0181150 A1 | 9/2004 | Evans et al. | |
| 2004/0181238 A1 | 9/2004 | Zarbatany et al. | |
| 2005/0101984 A1 | 5/2005 | Chanduszko et al. | |
| 2005/0149097 A1 | 7/2005 | Regnell et al. | |
| 2005/0209579 A1 | 9/2005 | Yacoubian et al. | |
| 2006/0009737 A1 | 1/2006 | Whiting et al. | |
| 2006/0135962 A1 | 6/2006 | Kick et al. | |
| 2006/0173440 A1 | 8/2006 | Lamson | |
| 2006/0247750 A1 | 11/2006 | Seifert et al. | |
| 2007/0021767 A1 | 1/2007 | Breznock | |
| 2007/0203515 A1 | 3/2007 | Heuser et al. | |
| 2008/0082136 A1 | 4/2008 | Gaudini | |
| 2008/0125748 A1 * | 5/2008 | Patel | A61M 25/0084 604/509 |
| 2008/0154172 A1 | 6/2008 | Mauch | |
| 2008/0171944 A1 * | 7/2008 | Brenneman | A61B 17/11 600/509 |
| 2008/0215008 A1 | 9/2008 | Nance et al. | |
| 2008/0228171 A1 * | 9/2008 | Kugler | A61B 17/221 604/529 |
| 2008/0249565 A1 | 10/2008 | Michler et al. | |
| 2009/0112050 A1 | 4/2009 | Farnan et al. | |
| 2009/0240122 A1 | 9/2009 | Avitsian | |
| 2010/0249491 A1 | 9/2010 | Farnan et al. | |
| 2011/0178530 A1 | 7/2011 | Bly | |
| 2011/0295206 A1 | 12/2011 | Gurley | |
| 2012/0136247 A1 | 5/2012 | Pillai | |
| 2012/0136366 A1 | 5/2012 | Pillai | |
| 2013/0006282 A1 | 1/2013 | Wilkinson | |
| 2013/0072957 A1 * | 3/2013 | Anderson | A61B 17/22 606/191 |
| 2013/0317528 A1 * | 11/2013 | Anderson | A61M 25/0136 606/159 |
| 2013/0324901 A1 | 12/2013 | Pillai | |
| 2013/0324967 A1 * | 12/2013 | Pillai | A61M 25/09 604/506 |
| 2014/0018837 A1 * | 1/2014 | Zhou | A61M 25/0155 606/194 |
| 2014/0142418 A1 | 5/2014 | Gurley et al. | |
| 2014/0142677 A1 | 5/2014 | Heuser et al. | |
| 2015/0320357 A1 | 11/2015 | Kauaguntla et al. | |
| 2017/0035591 A1 | 2/2017 | De Pablo et al. | |
| 2017/0056625 A1 | 3/2017 | Pillai | |
| 2019/0321600 A1 | 10/2019 | Pillai | |
| 2020/0069919 A1 | 3/2020 | Pillai | |

FOREIGN PATENT DOCUMENTS

| | | |
|---|---|---|
| WO | 2011068540 | 6/2011 |
| WO | 2013119547 | 8/2013 |

OTHER PUBLICATIONS

Office Action dated Aug. 29, 2019 for U.S. Appl. No. 15/835,114.
Office Action dated Jan. 30, 2018 for U.S. Appl. No. 14/949,243.
Office Action dated May 30, 2017 for U.S. Appl. No. 14/949,243.
Faul, et al., Vascular Disease Management, vol. 5 No. 5 , Sep./Oct. 2008 , 128-133.
Huang, et al., Evaluation of the Needle Technique for Producing an Arteriovenous Fistula, Journal of Applied Physiology, vol. 77(6) , Dec. 1994 ,2907-2911.
Khanna, et al., sharpening of Hollow Silicon Microneedles to Reduce Skin Penetration Force, , Mar. 15, 2010 ,045011.
Lumend Inc., et al., Outback LTD Re-Entry Catheter; Product Resources (http://www.lumend.com/Images/Technology/Products/brochure.pdf), , Jul. 19, 2006.
Mewissen, et al., Revascularization of Long FP Arterial Occlusions, Endovascular Today , Mar. 2004 ,2-4.
O'Callaghan, et al., Dynamics of Stab Wounds: Force Required for Penetration of Various Cadaveric Himan Tissues, Forensic Sci. Int'l., vol. 104 , Oct. 11, 1999 , 173-178.
Notice of Allowance dated Jan. 28, 2019 for U.S. Appl. No. 14/949,243.
Notice of Allowance dated Mar. 19, 2019 for U.S. Appl. No. 15/464,055.
Office Action dated Sep. 7, 2018 for U.S. Appl. No. 15/347,478.
Office Action dated Sep. 27, 2018 for U.S. Appl. No. 15/464,055.
Office Action dated Oct. 2, 2018 for U.S. Appl. No. 14/949,243.
Office Action dated Jun. 14, 2018 for U.S. Appl. No. 14/949,243.
Notice of Allowance dated Feb. 5, 2020 for U.S. Appl. No. 15/835,114.
Office Action dated Feb. 2, 2021 for U.S. Appl. No. 15/855,672.
Office Action dated Jun. 22, 2021 for U.S. Appl. No. 15/855,672.
Office Action dated Sep. 30, 2021 for U.S. Appl. No. 16/503,983.
Office Action dated Oct. 1, 2021 for U.S. Appl. No. 15/855,672.

\* cited by examiner

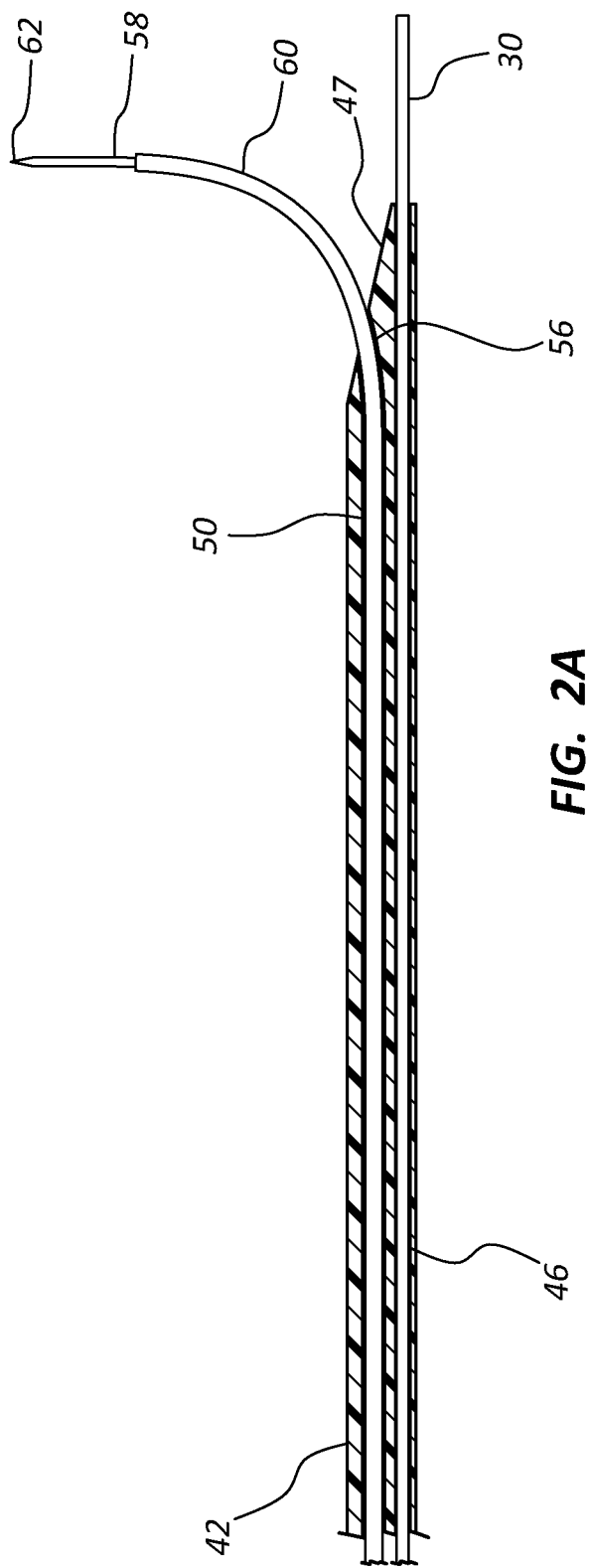
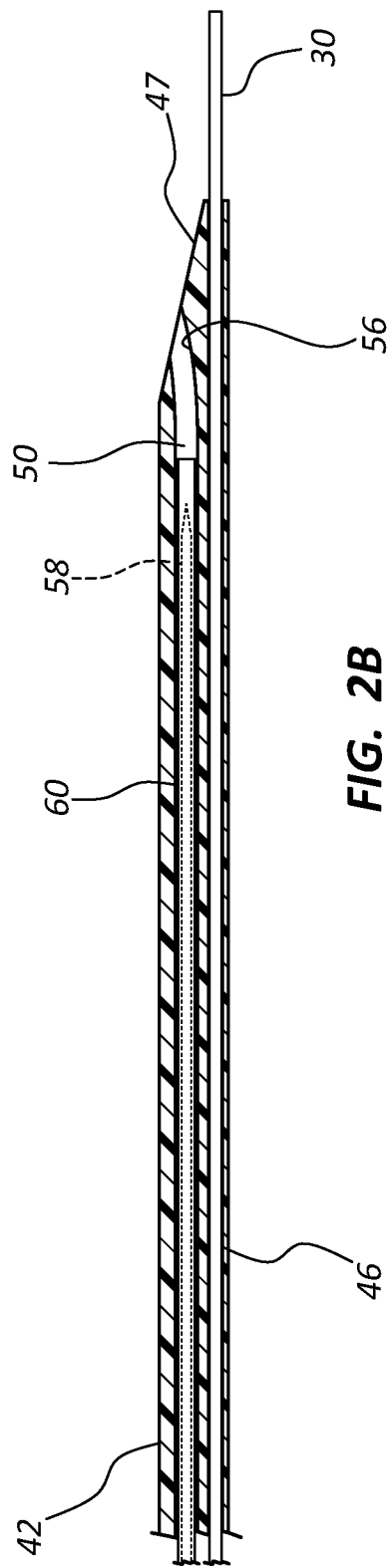

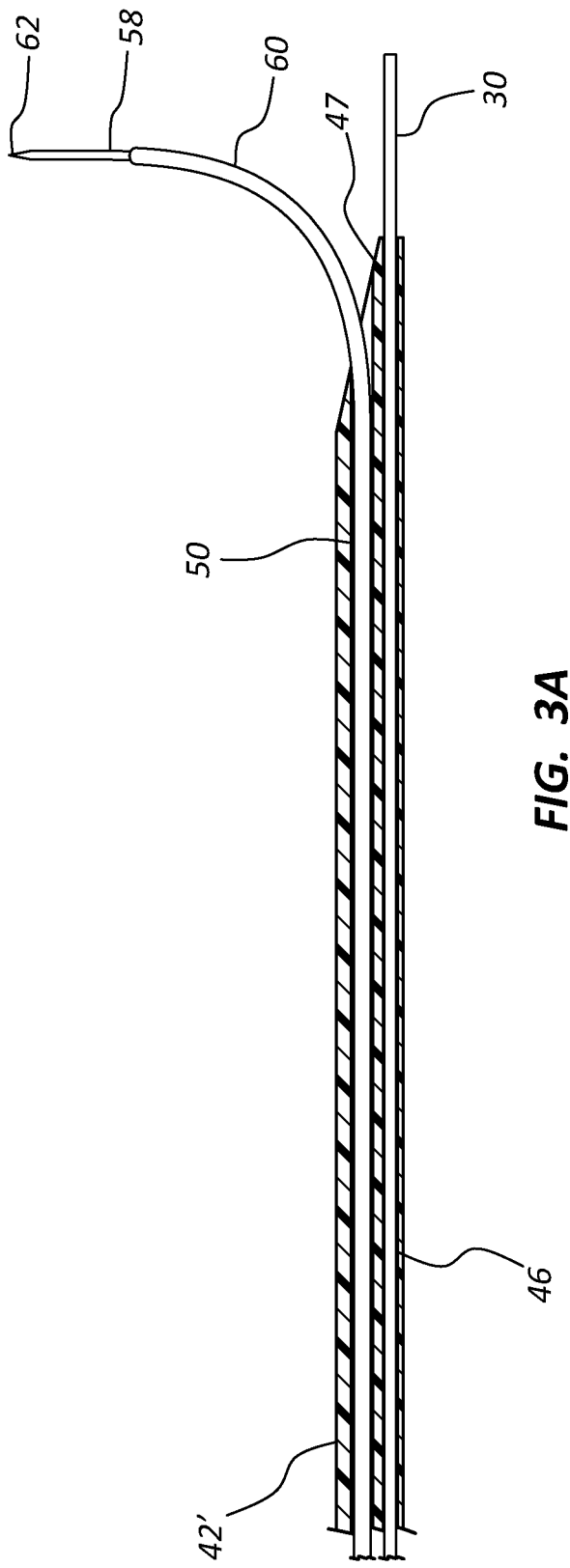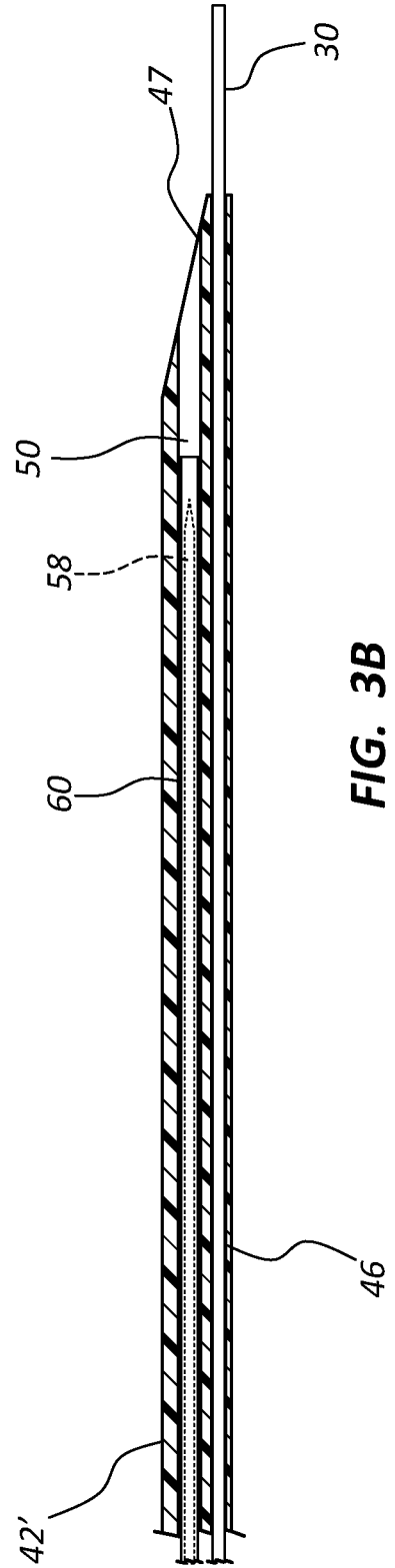

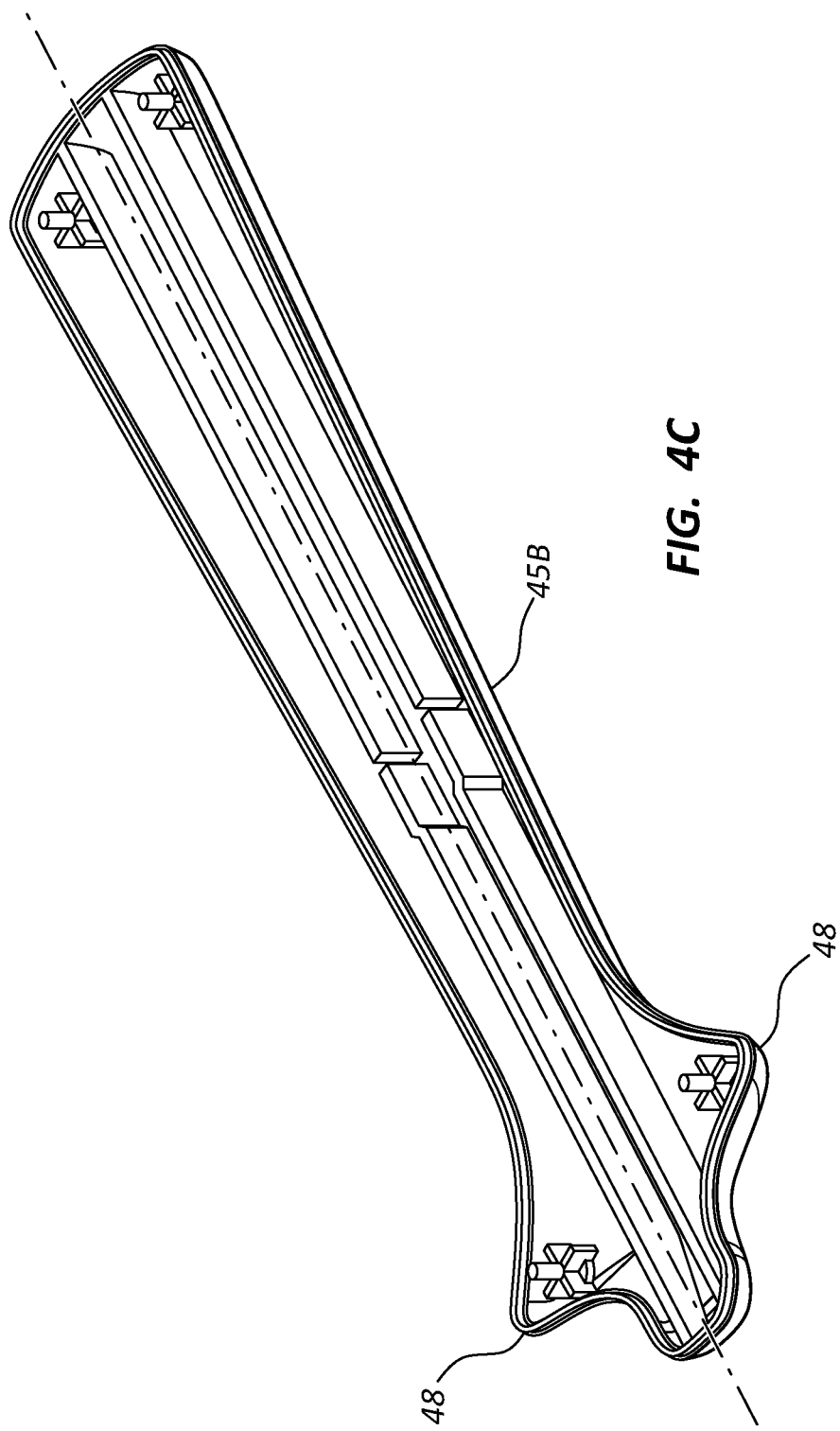

METHODS AND DEVICES FOR VASCULAR ACCESS

RELATED CASES

This application claims priority to U.S. Provisional Application No. 62/432,359, filed on Dec. 9, 2016 and titled "METHOD AND DEVICE FOR PERFORMING SUBINTIMAL ANGIOPLASTY," which is hereby incorporated by reference in its entirety.

TECHNICAL FIELD

The present disclosure relates to devices and methods for vascular access, including the treatment of patients with vascular disease. More specifically, in some embodiments, the present disclosure relates to devices and methods to treat patients with occluded peripheral arteries, including treatments comprising subintimal angioplasty techniques.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2A is a side view of a cross-section of a portion of the access device of FIG. 1 in a first configuration with an extended guide tube and stylet, the access device comprising a ramped surface.

FIG. 2B is a side view of a cross-section of a portion of the access device of FIG. 1 in a second configuration with a retracted guide tube and stylet, the access device comprising a ramped surface and.

FIG. 3A is a side view of a cross-section of a portion of another embodiment of an access device in a first configuration with an extended guide tube and stylet.

FIG. 3B is a side view of a cross-section of a portion of the access device of FIG. 3A in a second configuration with a retracted guide tube and stylet.

FIG. 4C is a perspective view of a bottom portion of the handle of the access device of FIG. 1.

DETAILED DESCRIPTION

Figure 1:
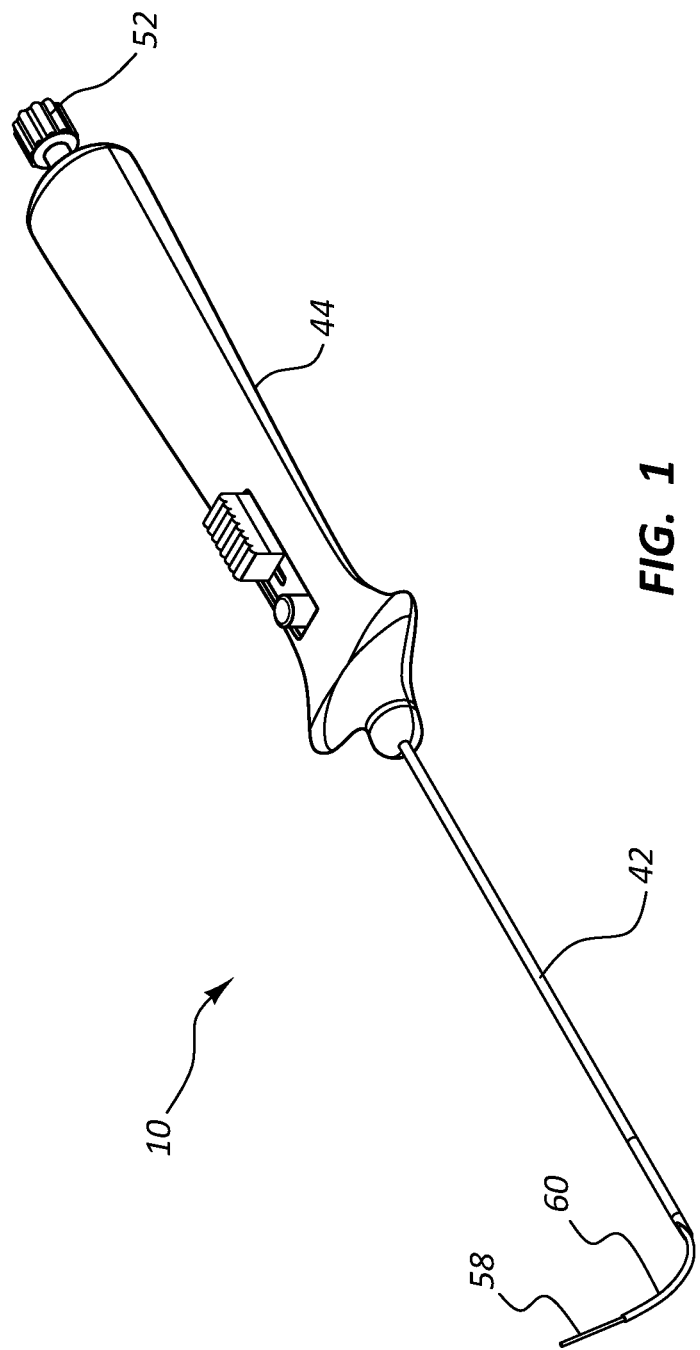
FIG. 1 is a perspective view of an access device.

The present disclosure describes access devices and methods for providing a second entry point to a vessel, the second entry point remote from a first entry point. The devices and methods of the present disclosure may be used to treat occlusive peripheral vascular disease by facilitating subintimal angioplasty. In some embodiments, access devices within the scope of this disclosure include systems comprising: a vascular catheter having first and second lumens, the first lumen being adapted to receive a vascular guidewire; a guide tube disposed in the second lumen, the guide tube having a distal end with a preformed curve; a stylet disposed in the guide tube, the stylet having a sharp distal tip configured to pierce vascular tissue; a guide tube actuator operatively connected to the guide tube or vascular catheter, the guide tube actuator configured to produce relative movement between the guide tube and the vascular catheter; and a stylet actuator operatively connected to the stylet, the stylet actuator having a stylet advancement mechanism. Access devices within the scope of this disclosure may provide a system for accessing an artery beyond an occlusion and forming a blood flow lumen through subintimal space along the occlusion.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In the following disclosure, various features are sometimes grouped together in a single embodiment, figure, or description thereof for the purpose of streamlining the disclosure. Many of these features may be used alone and/or in combination with one another. The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during normal use. The proximal end refers to the opposite end, or the end nearest the practitioner during use. As specifically applied to the access device of the present disclosure, the proximal end of the access device refers to the end nearest the handle and the distal end refers to the opposite end, the end nearest the tip of the catheter. Further, if at one or more points in a procedure a physician changes the orientation of an access device, as used herein, the term "proximal end" always refers to the handle end of the access device (even if the distal end is temporarily closer to the physician).

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

FIGS. 1-5C show various embodiments of devices for treating an occlusion in a blood vessel. For example, the devices disclosed in FIGS. 1-6B may be used in performing subintimal angioplasty. The devices shown in FIGS. 1-5C and described in the present disclosure are similar to those shown in U.S. Pat. No. 9,220,874, the disclosure of which is incorporated herein by reference. As indicated above, FIGS. 1-5C are not necessarily drawn to scale.

Referring to FIG. 1, an access device 10 may comprise a vascular access catheter or first catheter 42, a handle or actuator 44, a guide tube or cover tube 60, and a stylet 58. The access catheter 42 may be coupled to and extend from the handle 44. The length and diameter of the access catheter 42 may depend on a treatment or anatomy for which the access catheter 42 is intended for use. For example the length of the access catheter may be configured to traverse the distance between a desired entry point into an artery and the location of an occluded portion of the artery. In some embodiments, the length of the access catheter 42 may range from 20 cm to 150 cm, including from 50 cm to 100 cm. The diameter of the access catheter 42 may range from 5 Fr to 9 Fr, including from 6 Fr to 8 Fr.

Referring to FIGS. 2A-3B, which illustrate a portion of the access device 10 comprising a distal portion of the access catheter 42 in FIGS. 2A and 2B and an analogous portion of an alternative embodiment of an access catheter 42' in FIGS. 3A and 3B. The access catheters 42 and 42' are shown in cross-section, while the elements disposed within the access catheters are not in cross-section for clarity. The access catheter 42' of FIGS. 3A and 3B is identical to access the catheter 42 of FIGS. 2A and 2B except that access catheter 42' does not comprise a ramped surface as further detailed below. Accordingly, other elements of the access device of FIG. 1 as shown in FIGS. 3A and 3B (such as guidewire 30) retain the same numerals as the embodiment of FIGS. 1, 2A and 2B. Disclosure recited in connection with access catheter 42 of FIGS. 2A and 2B may be analogously applied to access catheter 42' of FIGS. 3A and 3B.

With continued reference to FIGS. 2A-3B as well as the access device of FIG. 1, the access catheter 42 may comprise a guidewire lumen 46 and a stylet lumen 50. In some embodiments, the guidewire lumen 46 and the stylet lumen 50 may be configured as a single lumen. The guidewire lumen 46 may be sized to receive any suitably sized guidewire, such as 0.014 inch, 0.018 inch, 0.035 inch, etc. The guidewire lumen 46 may be configured as a rapid exchange (RX) guidewire lumen for receiving a guidewire 30. For example, the guidewire lumen 46 may comprise a port adjacent a proximal portion that is configured to receive the guidewire 30. In other embodiments, a wall of the guidewire lumen 46 may be slit adjacent the proximal portion such that the guidewire 30 can be slipped into the guidewire lumen 46 via the slit. Further, in certain embodiments, the guidewire lumen 46 may extend to a proximal end of the access catheter 42 and the guidewire 30 may be advanced through a port (not shown) of the handle 44 into the guidewire lumen 46. Additionally, the guidewire 30 can be introduced into the guidewire lumen 46 using an introducer kit (not shown).

The stylet lumen 50 may extend from the handle 44 to an opening 54 adjacent the distal end of the access catheter 42. In some embodiments, the stylet lumen 50 curves or is ramped at its distal end to form a camming surface 56 as shown in the embodiment of FIGS. 2A and 2B. The camming surface 56 can provide additional structural support and curving guidance to the guide tube 60 when the guide tube 60 is advanced into an extended position. In some embodiments the stylet lumen 50 does not have a curved camming surface. For example, the stylet lumen 50 can be substantially straight adjacent its distal end as illustrated in the embodiment of FIGS. 3A and 3B.

The access catheter 42 comprises a catheter tip 47 at the distal end of the access catheter 42. The catheter tip 47 may be tapered, beveled, conical, or comprise other shapes or structures. In some embodiments the catheter tip 47 includes a radiopaque marker configured to be visible under fluoroscopy. The radiopaque marker can be embedded in the catheter tip 47. In some embodiments the shape of the radiopaque marker can be selected to facilitate fluoroscopic identification of the location and orientation of the catheter tip 47. Examples of radiopaque marker materials include gold, platinum, platinum-iridium, and other biocompatible radiopaque materials.

The guide tube 60 may be concentrically disposed within the stylet lumen 50 of the access catheter 42. The guide tube 60 may be operatively coupled to the handle 44 and extend from the handle 44 toward the distal end of the access catheter 42. A distal end of the guide tube 60 may be positioned adjacent the catheter tip 47 prior to actuation of the handle 44 as illustrated in the configurations of FIGS. 2B and 3B. In some embodiments, the guide tube 60 may extend beyond the catheter tip 47 following actuation of the handle 44, such as in the configurations shown in FIGS. 2A and 3A. In other embodiments, the guide tube 60 may not extend beyond the catheter tip 47 following actuation of the handle 44, such as embodiments wherein the stylet 58 extends beyond the catheter tip 47 (as further detailed below) but the guide tube 60 remains within the stylet lumen 50 after actuation.

As illustrated in FIGS. 2A and 3A, in some embodiments, the guide tube 60 comprises a preformed curve or bend of substantially 90 degrees at the distal end of the guide tube 60. The range of the angle of the curve or bend may be from 15 degrees to 120 degrees, including 75 degrees to 105 degrees. In some embodiments, a camming surface 56 of the stylet lumen 50 (see the embodiment of FIGS. 2A and 2B) can promote the curvature of the guide tube 60.

The guide tube 60 may be formed of any suitable material such as nickel titanium, shape memory metal, superelastic metal, stainless steel, thermal plastic, etc. The outside diameter of the guide tube 60 may be configured such that the guide tube 60 can be slidably disposed within the stylet lumen 50. The inside diameter of the guide tube 60 may be configured such that a stylet 58 can be slidably disposed within the guide tube 60. For example, the guide tube 60 may be a nitinol hypotube having an outer diameter of 0.025 inch and an inside diameter greater than 0.014 inch such that an 0.014 inch diameter stylet can be disposed with the guide tube 60.

In some embodiments, the stylet 58 may be concentrically disposed within the guide tube 60. The stylet 58 may be operatively coupled to the handle 44 and extend from the handle 44 toward the distal end of the access catheter 42. A distal end of the stylet 58 may be positioned adjacent the distal end of the guide tube 60 prior to actuation of the handle 44 as illustrated in FIGS. 2B and 3B. In some embodiments, the stylet 58 may extend beyond the distal end of the guide tube 60 following actuation of the handle 44 as illustrated in FIGS. 2A and 3A.

The stylet 58 may comprise a sharp distal point 62 adapted to penetrate tissue and other material, such as blood vessel walls and occlusions. The sharp distal point 62 may comprise any suitable design, such as faceted, pencil point, etc. The stylet 58 may be formed of any suitable material such as nickel titanium, shape memory metal, superelastic metal, stainless steel, thermal plastic, etc. The outside diameter of the stylet 58 may be configured such that the stylet 58 can be slidably disposed within the guide tube 60. For example, the stylet 58 may be a nitinol wire having an outer diameter of 0.014 inch.

Figure 4A:
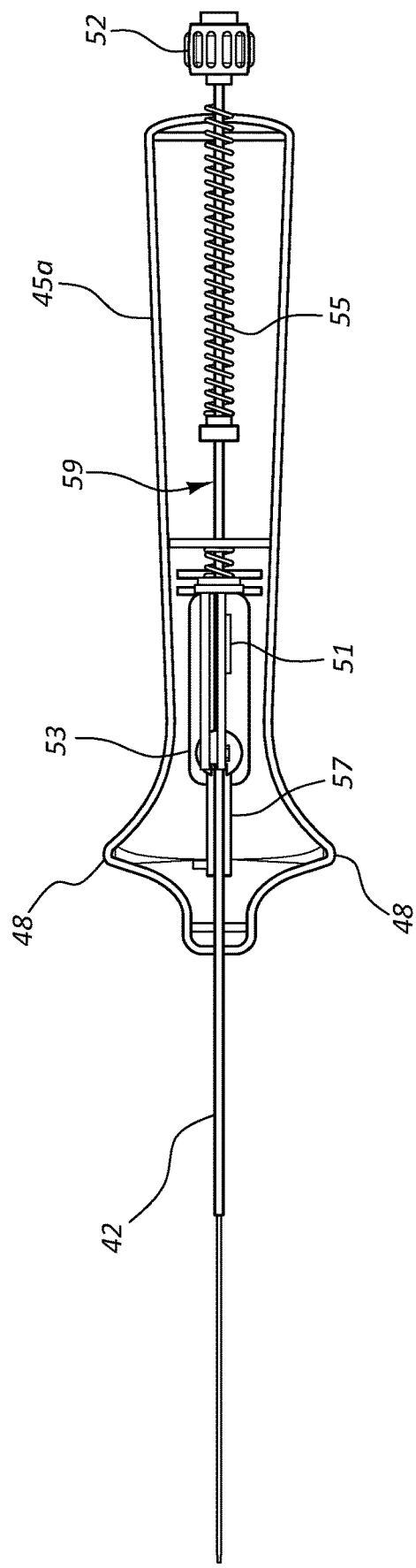
FIG. 4A is a bottom view of the access device of FIG. 1 with a portion of the handle removed to show internal components.
Figure 4B:
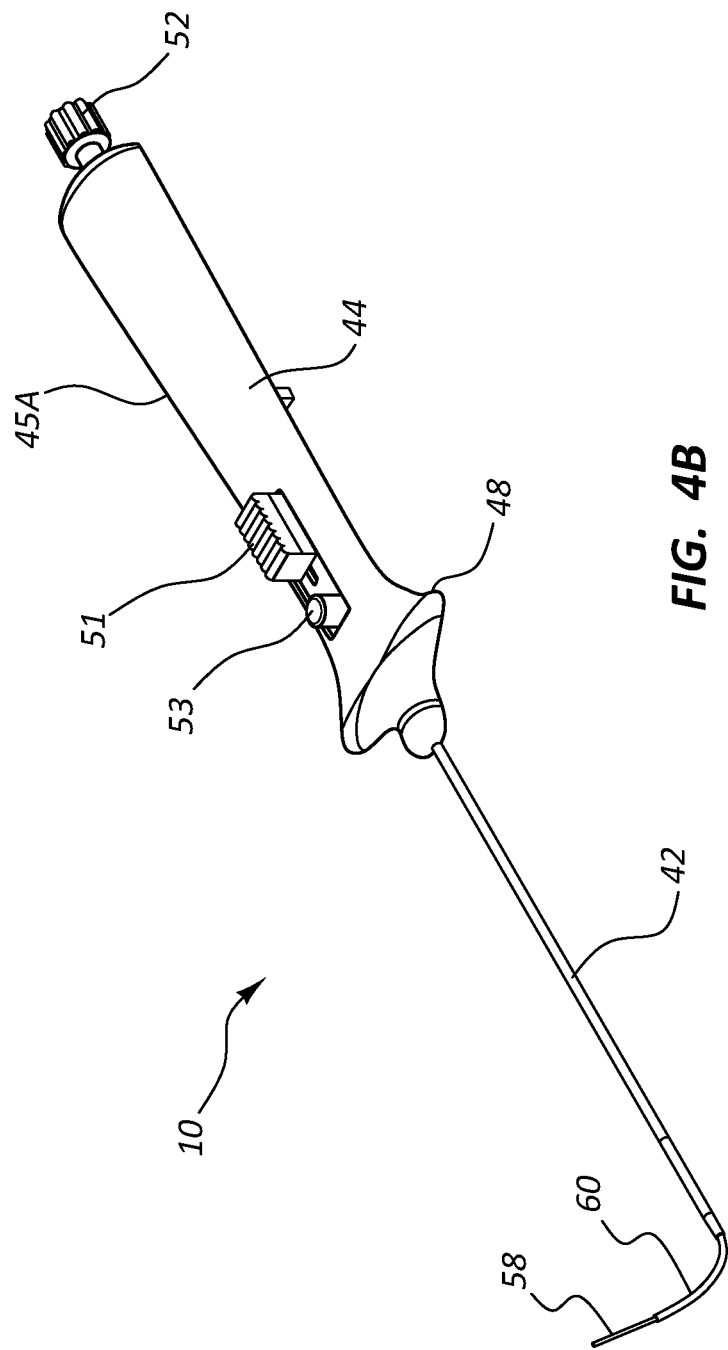
FIG. 4B is a perspective view of a top portion of the handle and other components of the access device of FIG. 1 configured with the guide tube and stylet advanced.

Referring to FIGS. 4A-4C, in some embodiments the handle 44 can comprise a top portion 45A, a bottom portion 45B, a slide button 51, and a stylet actuator 59. FIG. 4A is a bottom view of the handle 44 with the bottom portion 45B removed to show internal components and the inside of the top portion 45A. FIG. 4B illustrates top view of the handle 44 configured with the guide tube 60 and stylet 58 advanced. FIG. 4C illustrates the bottom portion 45B of the handle 44.

The top portion 45A and bottom portion 45B can engage to form the handle 44. The handle 44 may comprise wings 48 on opposing sides of the handle 44. The wings 48 can be used to apply a distal force to the access catheter 42 from the handle 44 and/or to otherwise manipulate the device.

In some embodiments, a proximal end of the access catheter 42 may be operatively coupled to the slide button 51 via a catheter slide 57. In use, the slide button 51 and catheter slide 57 may be displaced proximally causing the access catheter 42 to be displaced proximally such that the distal end of the guide tube 60 extends from the distal end of the access catheter 42 and assumes a curved shape. (As noted above, the guide tube 60 may be shape-set or otherwise biased to form a curved shape and assume that curved shape when unconstrained by the access catheter 42.) In other embodiments, a proximal end of the guide tube 60 may be operatively coupled to the slide button 51. In such embodiments, the slide button 51 may be displaced distally causing the guide tube 60 to be displaced distally such that the distal end of the guide tube 60 extends from the distal end of the access catheter 42 and assumes its curved shape as illustrated in FIG. 4B.

Figure 5A:
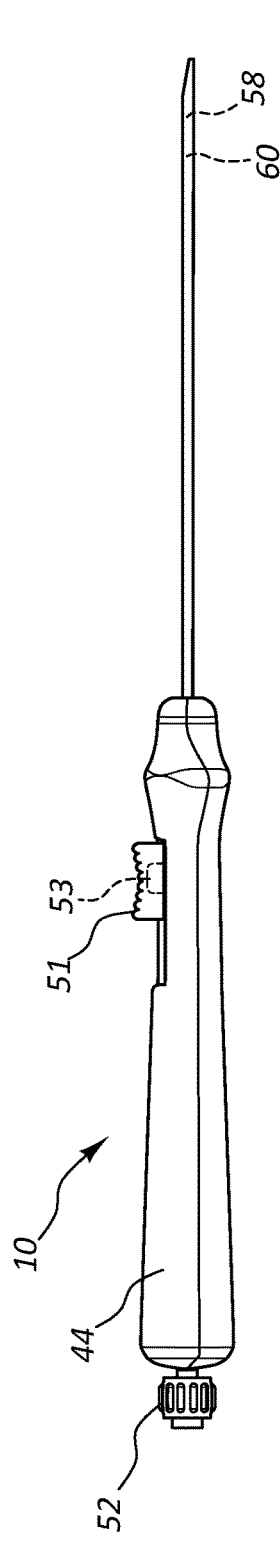
FIG. 5A is a side view of the access device of FIG. 1 prior to advancement of the guide tube.
Figure 5B:
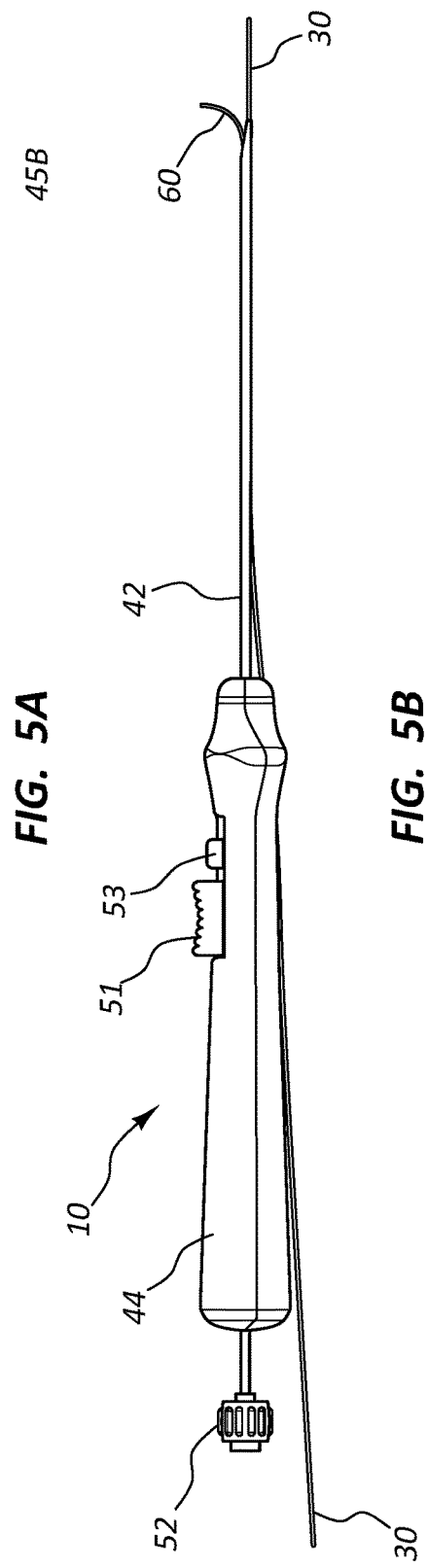
FIG. 5B is a side view of the access device of FIG. 1 following deployment of the guide tube and loading of a spring loading mechanism.
Figure 5C:
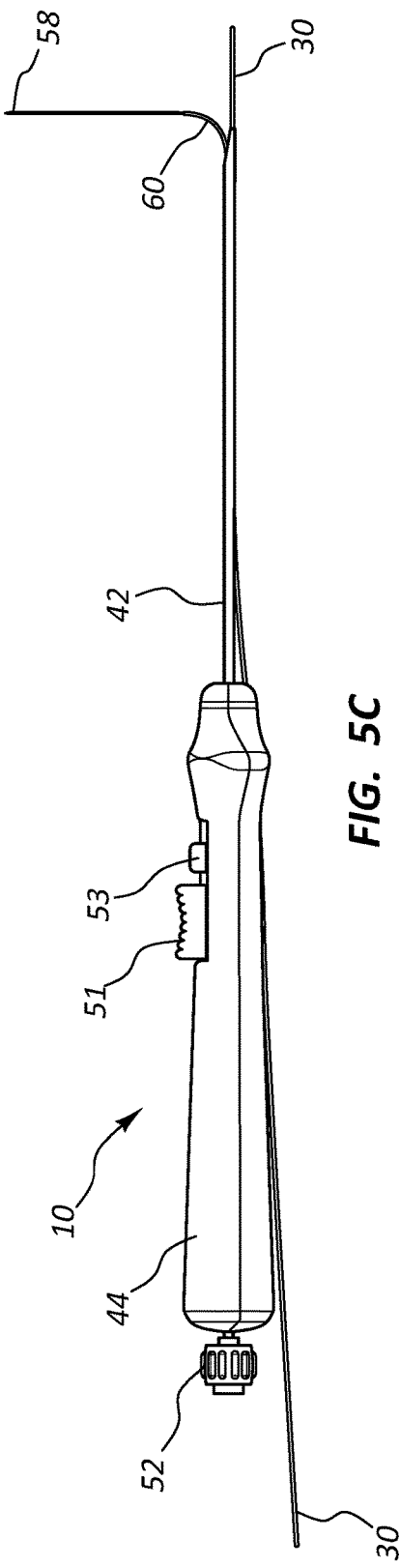
FIG. 5C is a side view of the access device of FIG. 1 following deployment of the stylet.

Referring to FIGS. 5A-5C as well as the components shown in FIG. 4, in certain embodiments, a proximal portion of the stylet 58 may be operatively coupled to the stylet actuator 59. The stylet actuator 59 may comprise a spring release button 53, a spring loading mechanism 52, and a spring 55 as illustrated in FIG. 4A. The stylet actuator 59 may be configured to displace the stylet 58 such that the distal end of the stylet 58 is displaced through vessel wall tissue and into a vessel lumen. In use, the stylet actuator 59 can be loaded by displacing the spring loading mechanism 52 proximally such that the spring 55 is compressed and the spring loading mechanism 52 is releasably locked in a proximal position. The slide button 51 may cover the spring release button 53 when the access device 10 is in a pre-ready configuration as illustrated in FIG. 5A. The slide button 51 may be displaced proximally, as described previously, such that the spring release button 53 is exposed, such as the configuration shown in FIG. 5B. The spring release button 53 may be positioned either proximal to or distal to the slide button 51. Displacement of the spring release button 53 causes the spring 55 to decompress. The spring loading mechanism 52 is displaced distally as the spring 55 is decompressed. The stylet 58, which is coupled to the spring loading mechanism 52, is displaced distally such that the distal end of the stylet 58 extends from the distal end of the guide tube 60 as illustrated in FIG. 5C.

The access device 10 may be used to perform a variety of vascular procedures, such as transjugular vein carotid artery access, retrograde jugular vein access, bypass graft placement, subintimal angioplasty, etc.

Figure 6:
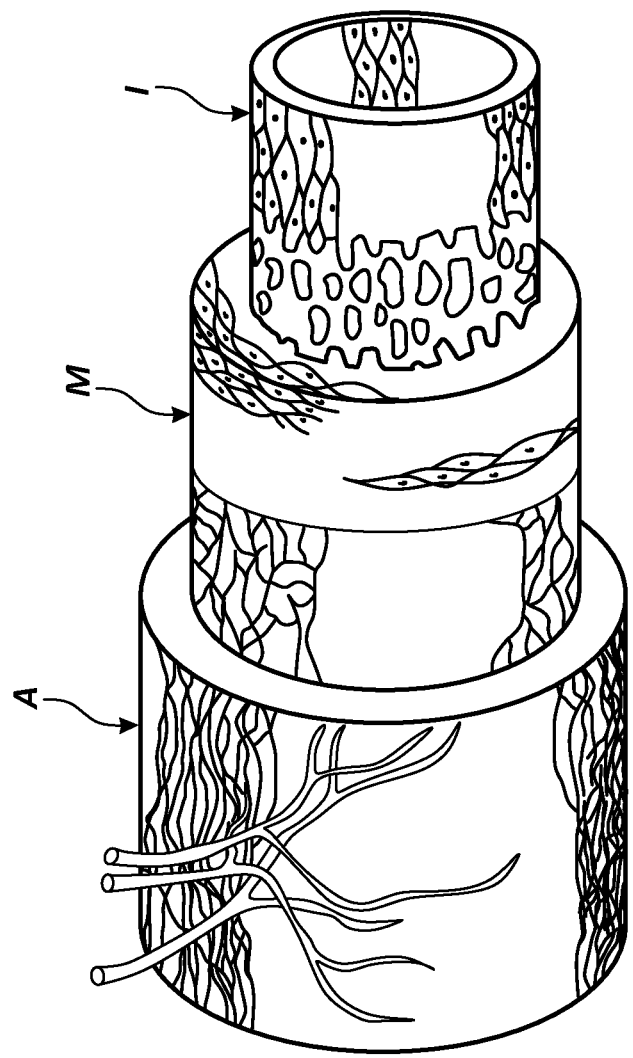
FIG. 6 is a perspective view of a sectioned artery wall.
Figure 7A:
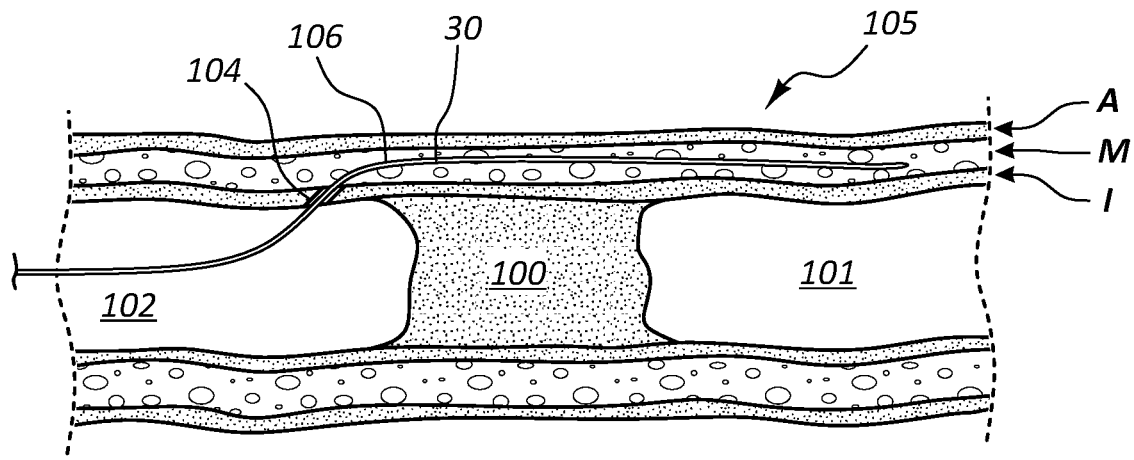
FIG. 7A is a cross-sectional view, taken through a plane including the longitudinal axis of the artery, of a portion of an artery showing a guidewire being advanced into a subintimal space of the artery along an occlusion.
Figure 7B:
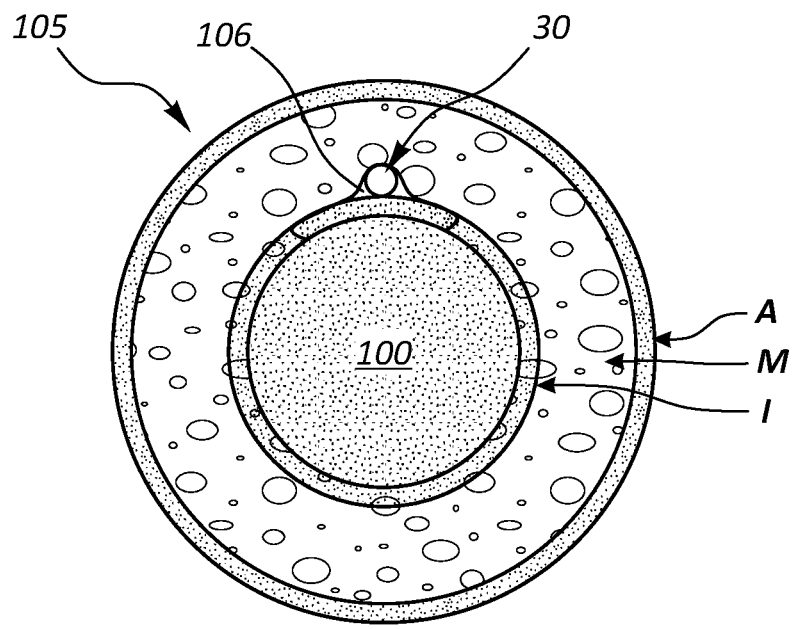
FIG. 7B is a cross-sectional view of a portion of the artery of FIG. 7A, taken through a plane perpendicular to the cross-sectional plan of FIG. 7A, showing the guidewire advanced into the intimal space along the occlusion.
Figure 7C:
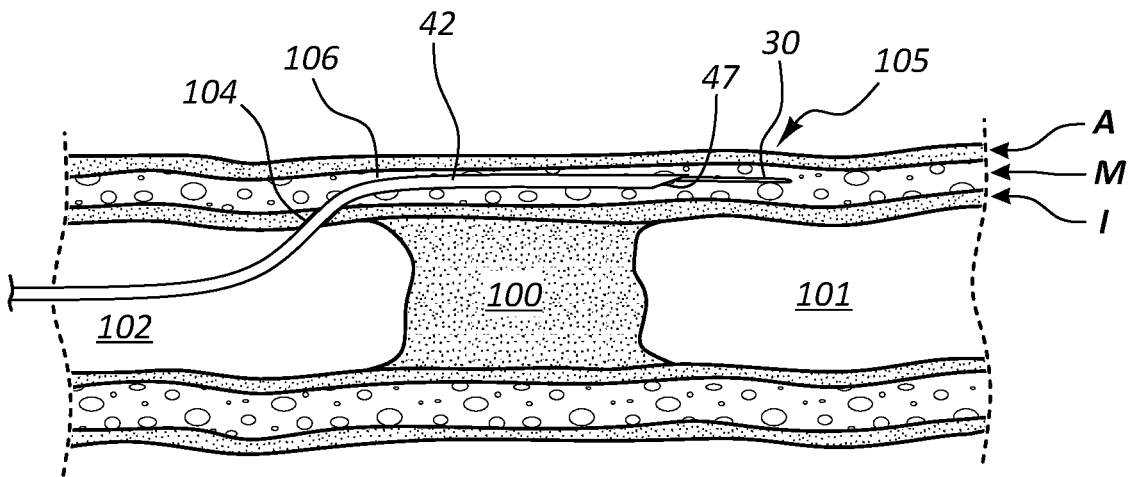
FIG. 7C is a cross-sectional view of the artery of FIG. 7A, taken through the cross-sectional plane of FIG. 7A, showing an access catheter of the access device of FIG. 1 within the subintimal space along the occlusion.
Figure 7D:
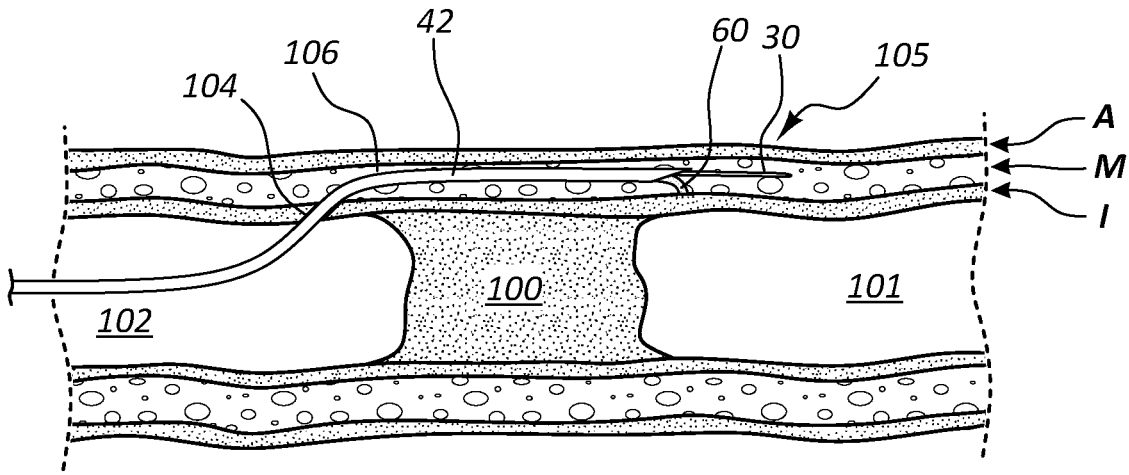
FIG. 7D is a cross-sectional view of the artery of FIG. 7A, taken through the cross-sectional plane of FIG. 7A, showing the guide tube of the access device deployed from a distal end of the access catheter.
Figure 7E:
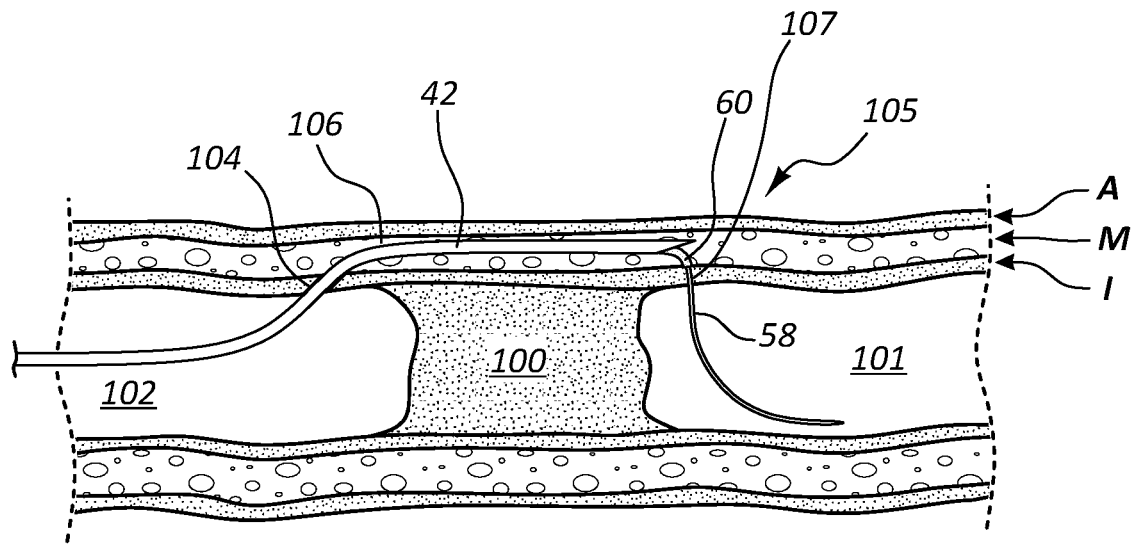
FIG. 7E is a cross-sectional view of the artery of FIG. 7A, taken through the cross-sectional plane of FIG. 7A, showing the stylet of the access device deployed from the guide tube into an arterial lumen beyond the occlusion.
Figure 7F:
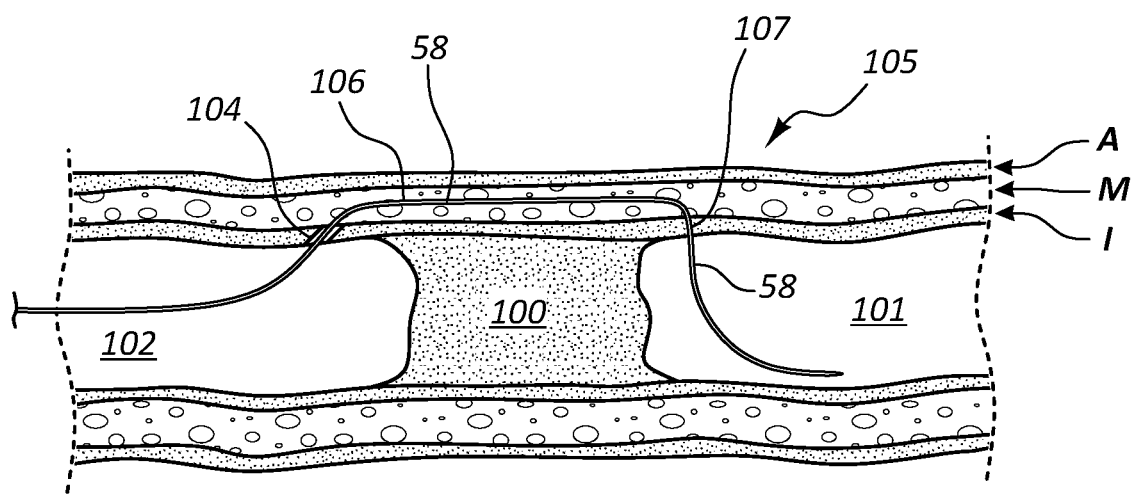
FIG. 7F is a cross-sectional view of the artery of FIG. 7A, taken through the cross-sectional plane of FIG. 7A, showing the stylet of the access device in the arterial lumen after removal of the access catheter.
Figure 7G:
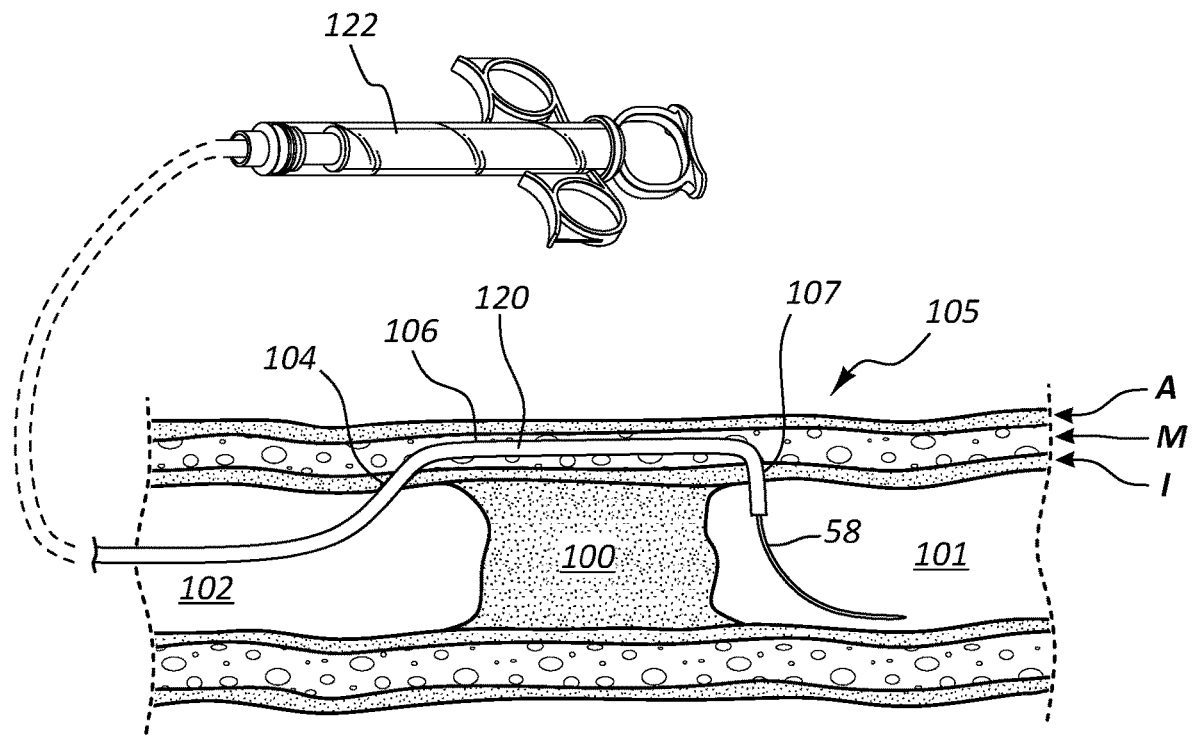
FIG. 7G is a cross-sectional view of the artery of FIG. 7A, taken through the cross-sectional plane of FIG. 7A, showing a distal end of a second catheter in the arterial lumen.
Figure 7H:
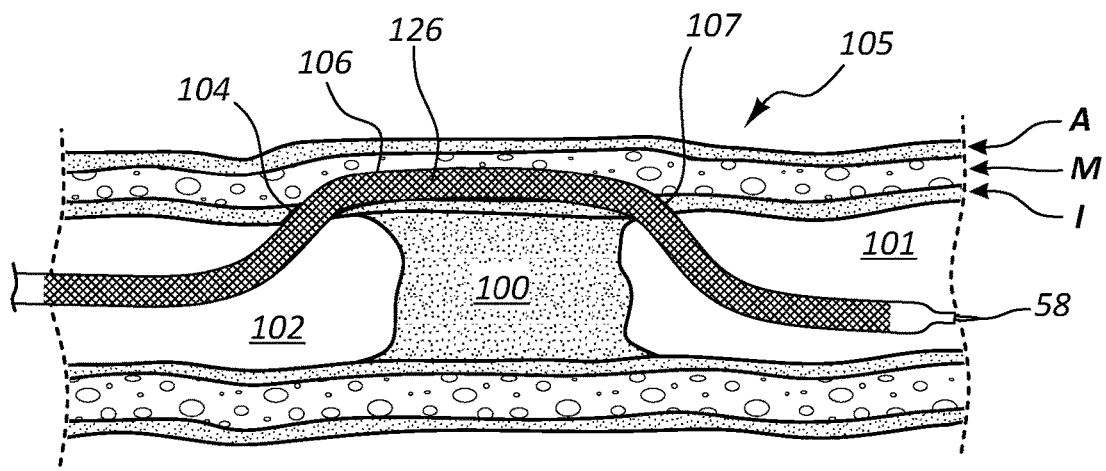
FIG. 7H is a cross-sectional view of the artery of FIG. 7A, taken through the cross-sectional plane of FIG. 7A, showing a distal end of a balloon in the arterial lumen and a stent within the subintimal space.
Figure 7I:
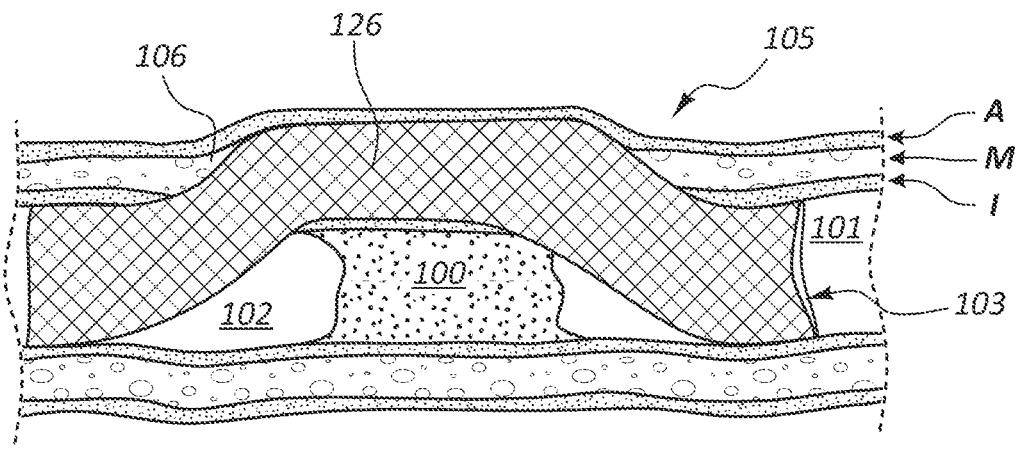
FIG. 7I is a cross-sectional view of the artery of FIG. 7A, taken through the cross-sectional plane of FIG. 7A, showing the expanded stent forming a blood flow lumen along the occlusion.

One exemplary procedure shown in FIGS. 6-7I is a subintimal angioplasty procedure to treat an occluded artery 105. FIGS. 7A-7I show the artery in cross-section with the elements of the access device disposed in various locations during the procedure. The access device is not shown in cross-section for clarity. The cross-sectional plane for FIGS. 7A and 7C-7I is a plane that includes the longitudinal axis of the artery, while the cross-sectional plane of FIG. 7B is a cross-sectional plane that cuts laterally across the artery, perpendicular to the plane of FIGS. 7A and 7C-7I.

Subintimal angioplasty procedures may be performed in various portions of the vasculature, including vasculature within a leg of a patient. As illustrated in FIG. 6 the wall of the artery to be treated is comprised of three layers. The inner layer is the tunica intima I. The middle layer is the tunica media T, which is the thickest layer. The outer layer is the tunica adventia A. These layers are labeled using the same designations in FIGS. 7A-7I.

As shown in FIGS. 7A-7B during the procedure, a guidewire 30 is inserted into a lumen 102 of the occluded artery 105 under fluoroscopic guidance. The guidewire 30 is directed to penetrate the tunica intima I and is advanced into a subintimal space 106 through a subintimal access site 104. The guidewire 30 is advanced further to reach beyond an occlusion 100, to the position shown in FIG. 7A. As illustrated in FIG. 7B the guidewire 30 creates and is disposed within a subintimal space 106 between the tunica intima I and tunica media M layers.

Referring to FIG. 7C, the access catheter 42 of the access device 10 may then be advanced over the guidewire 30 and positioned such that the catheter tip 47 is beyond the occlusion 100. In some embodiments, the guidewire 30 is removed through the guidewire lumen 46 of the access catheter 42. In other embodiments, the guidewire 30 remains in place.

Prior to advancing the guide tube 60, the access catheter 42 may be oriented such that the guide tube 60 will be directed toward the tunica intima I of the occluded artery 105. To help ensure that the guide tube 60 will be directed toward the tunica intima I and a portion of a lumen 101 beyond the occlusion 100, the orientation of the extended guide tube 60 can be determined based on the orientation of the handle 44. For example, in the illustrated embodiment of FIGS. 1 and 4A, the slide button 51 is substantially perpendicular to a plane defined by the opposing wings 48 that extends along a length of the handle 44 (the plane defined by the curve where the top portion 45A of the handle 44 contacts the bottom portion 45B of the handle 44). The guide tube 60 may be directed to curve in the same orientation as the slide button 51 when the guide tube 60 extends from the distal end of the access catheter 42 (see FIG. 4A). For example, if the slide button 51 is oriented upwards, the guide tube 60 will be oriented upwards as it extends from the access catheter 42. In certain embodiments, the orientation of the guide tube 60 may be visually verified. For example, fluoroscopy may be used to verify orientation of the guide tube 60. Further, as noted above, a radiopaque marker or other indicia may be used to verify the orientation of the access catheter 42.

With the access catheter disposed as shown in FIG. 7A, the slide button 51 is displaced proximally as shown in FIG. 5B, such that the guide tube 60 is displaced distally and extends from the access catheter 42. This results in the configuration shown in FIG. 7D. In some embodiments, the slide button 51 may be displaced proximally such that the access catheter 42 is displaced proximally and the guide tube 60 extends from the access catheter 42 in the pre-formed curve shape. As illustrated in FIG. 7D, the guide tube 60 may thus be directed toward the tunica intima I by the pre-formed curve at the distal end of the guide tube 60. In some embodiments, the guide tube 60 may be directed toward the tunica intima I by the camming surface 56 of the access catheter 42. In some embodiments, the distal end of the guide tube 60 is positioned adjacent the tunica intima I. In other embodiments, the distal end of the guide tube 60 may be disposed within the lumen 101.

The stylet actuator 59 may be loaded by proximally displacing the spring loading mechanism 52. The stylet actuator 59 may be activated by depressing the spring release button 53 of the handle 44. After actuation, the stylet 58 may then be disposed in the configuration shown in FIG. 7E. As shown in FIG. 7E, the distal end of the stylet 58 may penetrate the tunica intima I creating a subintimal exit site 107 and is displaced into the lumen 101.

Figure 7J:
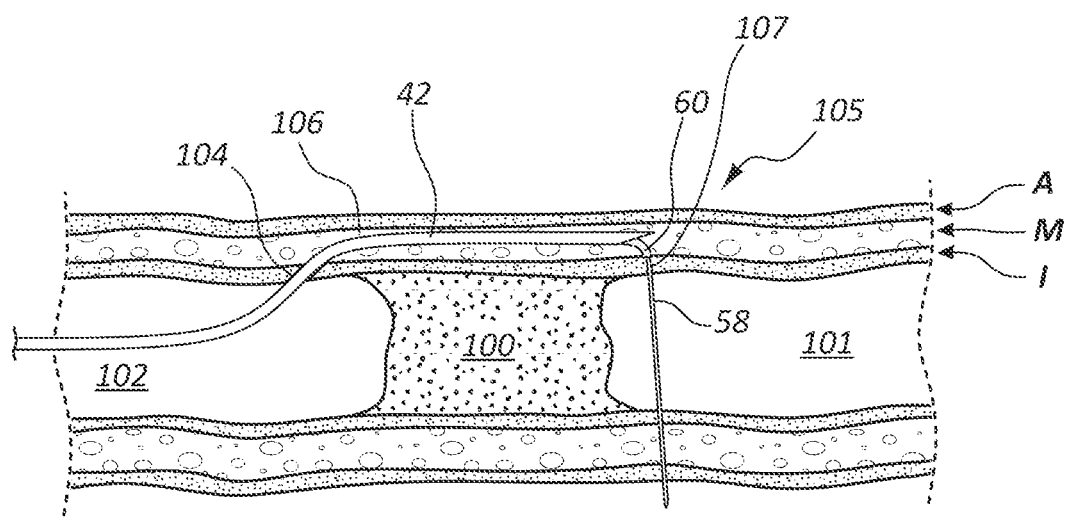
FIG. 7J is a cross-sectional view of the artery of FIG. 7A, taken through the cross-sectional plane of FIG. 7A, showing a distal end of the stylet disposed within tissue surrounding the artery.

The subintimal exit site 107 may be understood as second arterial access site with the first arterial access site being the site the artery 105 is accessed for insertion of the first catheter 42 into the artery 105. In some procedures, for example as shown in FIG. 7J, the distal end of the stylet 58 may penetrate the wall of the occluded artery 105 opposite the access catheter 42 such that the distal end of the stylet 58 may be disposed within tissue surrounding the occluded artery 105.

Referring to FIG. 7F, the stylet 58 may be decoupled from the handle 44 and the access catheter 42, and guide tube 60 may be withdrawn from the occluded artery 105 over the stylet 58. The stylet 58 is shown to enter the subintimal space 106 through the subintimal access site 104, extend through the subintimal space 106, and exit the subintimal space 106 through the exit site 107.

A second catheter 120 may be advanced over the stylet 58 such that the distal end of the second catheter 120 is disposed within the lumen 101 as shown in FIG. 7G. The second catheter 120 may be coupled to a syringe 122 such that blood may be aspirated through a lumen of the second catheter 120. The aspiration of blood through the second catheter 120 may be utilized to confirm that the distal end of the stylet 58 and the second catheter 120 are disposed within the lumen 101. In certain embodiments, an X-ray contrast dye may be injected through the second catheter 120 into the lumen 101 and visualized using fluoroscopy to show blood movement and thereby confirm proper placement of the stylet 58 and end of the second catheter 120. In some embodiments, the distal end of the stylet 58 may be disposed within tissue outside of the occluded artery 105. In such embodiments, the second catheter 120 may be partially withdrawn until blood is aspirated through the second catheter 120. The second catheter 120 may be withdrawn over the stylet 58 from the occluded artery 105.

Referring to FIG. 7H, a balloon catheter 125 comprising a stent 126 may be advanced into the occluded artery 105 over the stylet 58 such that a distal end of the balloon catheter 125 is disposed in the lumen 101. The proximal end of the stent 126 may be positioned within the lumen 102, a middle portion of the stent 126 may be within the subintimal space 106 and adjacent the occlusion 100, and a distal end of the stent 126 may be positioned within lumen 101.

Referring now to FIG. 7I, the stent 126 may be expanded such that a blood flow lumen 103 is formed through the expanded stent 126 from the lumen 101 to lumen 102 within the subintimal space 106. The occlusion 100 may be bypassed by the lumen 103 such that blood flows freely from the lumen 102 to the lumen 101. In some embodiments, the occlusion 100 may be at least partially compressed as the stent 126 is expanded.

Access to the lumen 101 as shown in FIGS. 7F and 7G can be used to perform various procedures, including inflation of an angioplasty balloon to compress the occlusion, deployment of stents in other locations, and/or access and therapies at locations beyond the occlusion.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A method of treating an occlusion in an artery, the method comprising:

advancing a guidewire into a lumen of the artery and into a subintimal space of a wall of the artery adjacent the occlusion;

advancing a first catheter over the guidewire into the subintimal space;

advancing a stylet guide from the first catheter toward a portion of the lumen of the artery beyond the occlusion such that a distal end of the stylet guide is substantially orthogonal to an inner layer of the wall of the artery;

operating a first actuator to move a stylet along a curved path through the stylet guide, wherein the distal end of the stylet guide remains in the subintimal space when the stylet is displaced into the portion of the lumen of the artery beyond the occlusion, and wherein a distal portion of the stylet guide comprises a preformed curve sized to be disposed within the subintimal space; and penetrating the inner layer of the wall of the artery from the subintimal space with a distal end of the stylet into the lumen of the artery beyond the occlusion, wherein the distal end of the stylet penetrates the wall of the artery opposite the first catheter such that the distal end of the stylet is disposed within tissue surrounding the artery.

2. The method of claim 1, wherein the first actuator is loaded by proximal displacement of a spring loading mechanism.

3. The method of claim 1, wherein operating the first actuator comprises releasing a spring coupled to the stylet.

4. The method of claim 1, wherein the stylet comprises a sharp distal end.

5. The method of claim 1, wherein the first catheter comprises a distal end comprising a ramped surface.

6. The method of claim 1, wherein the first catheter is coupled to a second actuator.

7. The method of claim 6, wherein the second actuator comprises a mechanism coupled to the stylet guide, wherein displacement of the mechanism displaces the stylet guide.

8. The method of claim 1, wherein the stylet is displaced distally relative to the stylet guide when operating the actuator.

9. The method of claim 1, further comprising:
orienting the first catheter such that the stylet guide is directed toward the portion of the artery beyond the occlusion when extended from the first catheter.

10. The method of claim 1, further comprising:
advancing a second catheter over the stylet, wherein a portion of the second catheter is within the subintimal space and a distal end of the second catheter is disposed within the portion of the lumen of the artery beyond the occlusion; and
aspirating blood through the second catheter to confirm that the distal end of the second catheter and the distal end of the stylet are disposed within the portion of the lumen of the artery beyond the occlusion.

11. The method of claim 1, further comprising:
advancing a balloon catheter comprising a stent over the stylet, wherein a portion of the stent is within the subintimal space adjacent the occlusion and a distal end of the balloon catheter is disposed within the portion of the lumen of the artery beyond the occlusion; and
expanding a balloon and the stent of the balloon catheter, wherein a bypass blood flow lumen is formed in the subintimal space adjacent the occlusion.

12. A method of performing subintimal angioplasty, the method comprising:
obtaining an access device comprising:

a handle;
a first actuator disposed within the handle comprising a spring mechanism; a first catheter coupled to the actuator;
a stylet guide comprising a curved distal end portion, wherein the stylet guide is concentrically disposed within the first catheter and longitudinally displaceable relative to the first catheter; and
a stylet concentrically disposed within the stylet guide and longitudinally displaceable relative to the stylet guide;

advancing a guidewire into a lumen of an artery and into a subintimal space of a wall of the artery adjacent an occlusion;

advancing the first catheter over the guidewire into the subintimal space;

advancing the stylet guide from the first catheter toward a portion of the lumen of the artery beyond the occlusion such that a distal end of the stylet guide is substantially orthogonal to an inner layer of the wall of the artery;

operating the first actuator to displace the stylet along a curved path through the stylet guide, wherein the distal end of the stylet guide remains in the subintimal space when the stylet is displaced into the portion of the lumen of the artery beyond the occlusion, and wherein a distal portion of the stylet guide comprises a preformed curve sized to be disposed within the subintimal space;

penetrating the inner layer of the wall of the artery from the subintimal space with a distal end of the stylet into the lumen of the artery beyond the occlusion;

decoupling the access device from the stylet;

advancing a balloon catheter comprising a stent over the stylet after decoupling the access device from the stylet, wherein a portion of the stent is within the subintimal space adjacent the occlusion and a distal end of the balloon catheter is disposed within the portion of the lumen of the artery beyond the occlusion; and expanding a balloon and the stent of the balloon catheter, wherein a bypass blood flow lumen is formed in the subintimal space adjacent the occlusion, wherein the distal end of the stylet penetrates the wall of the artery opposite the first catheter such that the distal end of the stylet is disposed within tissue surrounding the artery.

13. The method of claim 12, further comprising:
advancing a second catheter over the stylet guide and stylet, wherein a portion of the second catheter is within the subintimal space and a distal end of the second catheter is disposed within the portion of the lumen of the artery beyond the occlusion; and
aspirating blood through the second catheter to confirm that the distal end of the second catheter and the distal end of the stylet are disposed within the portion of the lumen of the artery beyond the occlusion.

14. The method of claim 12, wherein operating the first actuator comprises releasing the spring mechanism coupled to the stylet.

15. The method of claim 12, wherein the stylet comprises a sharp distal end.

16. The method of claim 12, wherein the first catheter comprises a distal end comprising a ramped surface.

17. The method of claim 12, wherein a second actuator comprises a sliding button coupled to the stylet guide, wherein displacement of the sliding button displaces the stylet guide.

18. The method of claim 17, wherein the preformed curve is aligned with the sliding button.

19. A method of accessing a lumen of an artery at a second access site, comprising:

percutaneously accessing a first portion of the lumen of the artery at a first access site; advancing a guidewire into the lumen of the artery and into a subintimal space of a wall of the artery;

advancing a catheter over the guidewire into the subintimal space;

advancing a guide tube from the catheter toward a second portion of the lumen of the artery such that a distal end of the guide tube is substantially orthogonal to an inner layer of the wall of the artery;

displacing a stylet relative to the guide tube, wherein the distal end of the guide tube remains in the subintimal space when the stylet is displaced into the second portion of the lumen of the artery, and wherein a distal portion of the guide tube comprises a preformed curve sized to be disposed within the subintimal space; and penetrating the inner layer of the wall of the artery from the subintimal space with a distal end of the stylet into the lumen of the artery through a second access site in the inner layer of the wall of the artery, wherein the distal end of the stylet penetrates the wall of the artery opposite the catheter such that the distal end of the stylet is disposed within tissue surrounding the artery.

20. The method of claim 19, wherein a first actuator advances the guide tube.

21. The method of claim 20, wherein a second actuator displaces the stylet.

22. The method of claim 19, wherein the lumen of the artery comprises an occlusion and the occlusion is disposed between the first access site and the second access site.

* * * * *